United States Patent [19]

Misaki et al.

[11] 4,237,222
[45] Dec. 2, 1980

[54] LACTATE OXIDASE PROCESS FOR THE MANUFACTURE THEREOF AND ANALYTICAL METHOD AND KIT FOR THE USE OF THE SAME

[75] Inventors: Hideo Misaki; Yoshifumi Horiuchi; Kazuo Matsuura; Saburo Harada, all of Shizuoka, Japan

[73] Assignee: Toyo Jozo Kabushiki Kaisha, Shizuoka, Japan

[21] Appl. No.: 49,560

[22] Filed: Jun. 18, 1979

[30] Foreign Application Priority Data

Jun. 17, 1978 [JP] Japan ................... 53-73619

[51] Int. Cl.$^2$ .................... C12Q 1/26; C12N 9/04
[52] U.S. Cl. ........................ 435/25; 435/190
[58] Field of Search ................... 435/25, 190

[56] References Cited

PUBLICATIONS

Thomas E. Barman, Enzyme Handbook, vol. 1, p. 111; 1969.
Yuichi Yamamura et al., Nature, "Lactic Oxidases of Mycobacterium tuberculosis avium", vol. 170, No. 4318, pp. 207–208; 1952.
The American Type Culture Collection Catalogues of Straine I, 13th Ed. pp. 26, 116, 149 and 150; 1978.

*Primary Examiner*—Robert J. Warden
*Attorney, Agent, or Firm*—Young & Thompson

[57] ABSTRACT

Novel enzyme lactate oxidase can be produced by culturing Pediococcus sp. B-0667, Streptococcus sp. B-0668, *Aerococcus viridans* IFO-12219 or *Aerococcus viridans* IFO-12317. It is useful for analysis for L-lactic acid, because it catalyzes the reaction of L-lactic acid and oxygen to form pyruvic acid and hydrogen peroxide. A kit containing the various reagents for such analysis is also provided by this invention.

10 Claims, 8 Drawing Figures

○ – ○ : ACETATE BUFFER AND DIMETHYLGLUTARATE-NaOH BUFFER
△ – △ : PHOSPHATE BUFFER
● – ● : TRIS-HCl BUFFER
▲ – ▲ : GLYCINE BUFFER

O—O: DIMETHYLGLUTARATE-NaOH BUFFER

△—△: PHOSPHATE BUFFER

●—●: TRIS-HCℓ BUFFER

○ — ○ : L-LACTIC ACID
● — ● : DL-LACTIC ACID
△ — △ : $H_2O_2$

O—O : L-LACTIC ACID
●—● : DL-LACTIC ACID
△—△ : PYRUVIC ACID

O—O : DL-LACTIC ACID
●—● : H$_2$O$_2$
△—△ : HUMAN SERUM
▲—▲ : HUMAN SERUM DL-LACTIC ACID

LACTATE OXIDASE PROCESS FOR THE MANUFACTURE THEREOF AND ANALYTICAL METHOD AND KIT FOR THE USE OF THE SAME

This invention relates to a novel enzyme lactate oxidase and a process for the manufacture of lactate oxidase and its use in quantitative analysis and a kit for such analysis.

Lactate oxidase [L-lactate: oxygen oxidoreductase, E.C. 1.1.3.2] is a hitherto-known enzyme which catalyzes a reaction of lactic acid and oxygen to form acetic acid, carbon dioxide and water:

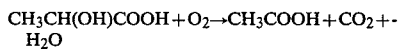

and has heretofore been derived from a strain of *Mycobacterium phlei* [E. Bakman, Enzyme Handbook, Vol. 1, p. 111, 1969] and *Mycobacterium avium* [Nature, 170, 207].

It has now been found that a novel enzyme lactate oxidase catalyzes a reaction of lactate to pyruvate and generates a stoichiometric amount of hydrogen peroxide, and that the said enzyme can be produced by culturing bacterial strains belonging to genus Pedoucoccus, genus Streptococcus and genus Aerococcus.

The novel enzyme lactate oxidase of the present invention has substantially different properties from the above prior known enzyme, and has the following substrate specificity and enzyme action:

Substrate specificity: L-lactic acid.

Enzyme action: catalyzes the following reaction [I]:

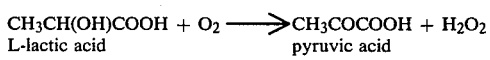

Optimum pH: about pH 6-7.

Optimum temperature: about 35° C.

Isoelectric point: pH 4.6±0.3 (measured by electrophoresis using carrier ampholite)

Molecular weight: 80,000±10,000 (gel filtration method using Sephadex G-150 [tradename])

The enzyme requires no addition of coenzymes in its reaction and catalyzes the direct reaction of a lactic acid substrate with oxygen by oxidizing one mole of lactic acid to pyruvate, forming one mole of hydrogen peroxide.

The novel enzyme lactate oxidase producing bacterial strains are referred to as Pediococcus sp. B-0667 and Streptococcus sp. B-0668. These strains were isolated from a soil sample collected in a radish field in Ohitocho, Tagata-gun, Shizuoka-ken, Japan.

The isolated strains B-0667 and B-0668 hereinabove have the following taxonomical properties.

| B. Microscopic observation: | | |
|---|---|---|
| | Strain B-0667 | Strain B-0668 |
| Shape: | Spherical, ovoid, pairs, tetra-shaped or short chain. | Spherical, ovoid, pairs, tetra-shaped or short chain. |
| Size: | 0.5–1.0 × 0.5–1.0 μ | 0.8–1.0 × 1.0–1.2 μ |
| Motility: | – | – |
| Spore: | – | – |
| Gram's stain: | + | + |
| Acid-fast stain: | – | – |

| C. Physiological properties: | | | |
|---|---|---|---|
| | | Strain B-0667 | Strain B-0668 |
| Growth temperature: | 45° C. | – | – |
| | 37° C. | + | + |
| | 30° C. | + | + |
| | 26° C. | + | + |
| | 5° C. | + | + |
| | 5° C. | ± or (+) | ± or (+) |
| Halotolerance: NaCl | 10% | + | – |
| | 6.5% | + | – |
| | 5.0% | + | + |
| | 1.0% | + | + |
| | 0% | + | – |
| OF-test: | | fermentative | fermentative |
| Behavior in oxygen: | | facultative anaerobic | facultative anaerobic |
| Nitrate reduction: | | – | – |
| Indole formation: | | – | – |
| Hydrogen sulfate formation: | | – | – |
| Gelatin hydrolysis: | | – | – |
| Starch hydrolysis: | | – | – |
| Esculin hydrolysis: | | + | + |
| Acetoin formation: | | – | – |
| MR-test: | | – | – |
| Catalase: | | – | – |
| Oxidase: | | – | – |
| Urease (SSR): | | – | – |
| Urease (Christensen): | | – | – |
| Utilization of citric acid (Christensen): | | – | – |
| Acid formation from sugar: | | | |
| adonitol: | | – | – |
| L(+)- arabinose: | | – | – |
| cellobiose: | | + | + |
| dulcitol: | | – | – |
| meso-erythritol: | | – | – |
| fructose: | | + | + |
| fucose: | | – | – |
| galactose: | | + | + |
| glucose: | | + | + |
| glycerol: | | – | – |
| inositol: | | – | – |
| inulin: | | – | – |
| lactose: | | + | + |
| maltose: | | + | + |
| mannitol: | | – | – |
| mannose: | | + | + |
| melezitose: | | – | – |
| melibiose: | | + | – |
| raffinose: | | + | – |

| A. Observations on various media, cultured at 30° C. for 2 days: | | |
|---|---|---|
| | Strain B-0667 | strain B-0668 |
| Tryptosoybroth: | weak growth, homogeneously turbid, later wooly precipitation. | weak growth, homogenously turbid, later wooly precipitation. |
| Tryptosoy agar slant: | weak growth, pale yellowish gray, no lustre. no production of soluble pigment. | weak growth, pale yellowish gray, no lustre. no production of soluble pigment. |
| Tryptosoy agar plate: | colony; small and flat. | colony; small and flat. |
| Gelatin slab: | growth along stabbed line. no gelatin liquefaction. | growth along stabbed line. no gelatin liquefaction. |
| BCP milk (14 days): | no change. | no change. |

| C. Physiological properties: | | |
| --- | --- | --- |
| | Strain B-0667 | Strain B-0668 |
| L(+)- rhamnose: | − | − |
| salicin: | (+) | − |
| L-sorbose: | − | − |
| sorbitol: | − | − |
| starch: | − | − |
| sucrose: | + | + |
| trehalose: | + | + |
| xylose: | − | − |
| Tolerance at 60° C. for 30 min. | − | + |

Consulting "Bergey's Manual of Determinative Bacteriology", 8th Ed., 1974 and S. T. Cowan and K. J. Steel, "Manual for the Identification of Medical Bacteria", Cambridge Press, 1974, the strain B-0667 and B-0668 having the taxonomical properties hereinabove, especially Gram positive cocci, catalase and oxidase negative, fermentative acid formation from glucose, and no gas formation from sugar (glucose), is referred to as belonging to genus Pediococcus and genus Streptococcus.

Comparison of these strains with the identification manual of the above references is as follows.
In table:
+ = positive more than 85%;
− = negative more than 85%;
d = varies among strains or species.

| | Strain B-0667 | Strain B-0668 | genus Pediococcus | genus Streptococcus |
| --- | --- | --- | --- | --- |
| Growth at 45° C. | − | − | + | d |
| Tolerance at 60° C. for 30 min. | − | + | − | d |
| Glycerol (acid formation) | − | − | − | d |
| Arabinose (acid formation) | − | − | + | d |
| Halotolerance (NaCl 10%) | + | − | + | − |

Hence the strain B-0667 will be referred to as genus Pediococcus or Streptococcus. Consulting the above "Manual for the Identification of Medical Bacteria" and J. Gen. Microbiol., 26, 185–197 (1961), the taxonomic properties of the strain B-0667 were almost identical with those of *Pediococcus urina-equi,* however the characteristics described in "Bergey's Manual of Determinative Bacteriology", 8th Ed., 1974 were slightly different therefrom. Therefore the strain B-0667 is referred to as genus Pediococcus and designated as Pediococcus sp. B-0667.

The strain B-0668 resembles genus Streptococcus rather than genus Pediococcus. Further consulting the "Manual for the Identification of Medical Bacteria", the strain B-0668 resembles *Streptococcus faecium* var. *durans,* however no taxonomic properties were described in "Bergey's Manual" and therefor it is impossible to make a detailed comparison. The strain B-0668, therefore, is referred to as Streptococcus sp. B-0668.

The strains B-0667 and B-0668 were deposited for permanent collection in the Institute for Microbial Industry and Technology, Agency of Industrial Science and Technology, M.I.T.I., Japan, as deposition numbers FERM-P No. 4438 and FERM-P No. 4439, respectively. IFO-12219 and IFO-12317 were deposited for permanent collection in the Institute for Fermentation, Osaka, Japan, under those numbers.

An object of the present invention is accordingly to provide a novel enzyme lactate oxidase, at least having a substrate specificity for L-lactic acid, which catalyzes a reaction of the formula [I]:

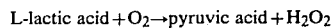

L-lactic acid + $O_2$ → pyruvic acid + $H_2O_2$

Another object of the present invention is to provide a process for the manufacture of novel enzyme lactate oxidase which comprises culturing a lactate oxidase-producing microorganism belonging to genus Pediococcus, Streptococcus or Aerococcus in a nutrient culture medium and isolating the lactate oxidase thus produced from the cultured medium.

A further object of the present invention is to provide a kit for quantitative analysis, especially a reaction system containing lactate oxidase.

A still further object of the present invention is to provide an analytical method for determining lactic acid in a sample containing lactic acid or a lactic acid liberating system, which method comprises treating a sample with a reaction system containing lactate oxidase and measuring a consumed component or generated component.

Other objects, feature and advantages of the present invention will become apparent from a consideration of the following description, taken in connection with the accompanying drawings, which are graphs illustrating the present invention, and in which more particularly:

Figure 1:
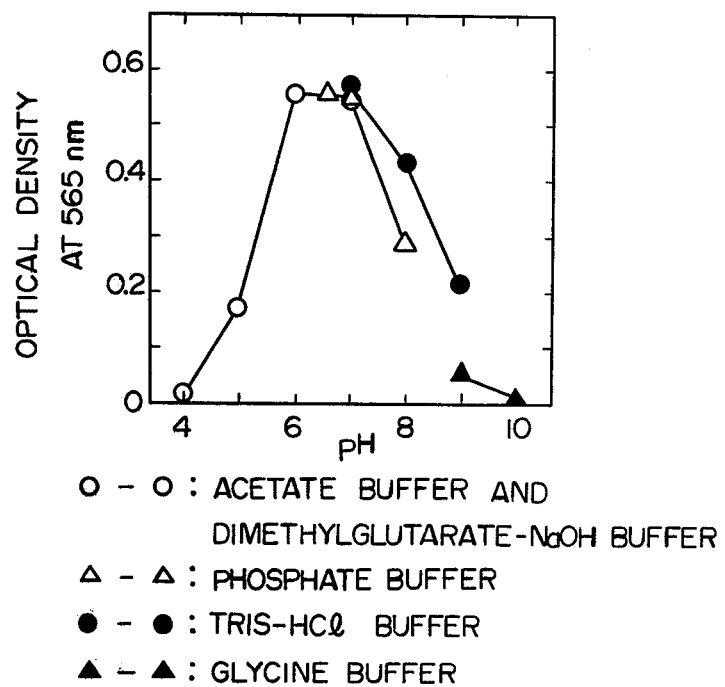
FIG. 1 shows the optimum pH of lactate oxidase of the present invention.

In an embodiment of the present invention, Pediococcus sp. B-0667, Streptococcus sp. B-0668, *Aerococcus viridans* IFO-12219 or *Aerococcus viridans* IFO-12317 are cultured in a conventional medium for enzyme production. Cultivation can be by conventional liquid culture and submerged aeration culture is preferable for industrial production.

A conventional medium for culturing microorganisms can preferably be used. For the carbon sources, assimilable carbon sources such as glucose, sucrose, lactose, maltose, fructose, molasses or the like can preferably be used. Assimilable nitrogen sources such as peptone, polypeptone, meat extract, yeast extract, casein hydrolyzate or the like can be used. Various inorganic salts such as phosphates, carbonates, sulfates, salts of magnesium, calcium, potassium, sodium, divalent iron, manganese or zinc can be used.

The culturing temperature can be selected within the range for growth of microbial cells and production of lactate oxidase, and is preferably 25°–37° C. The culturing time can be altered depending on conditions and is terminated when the lactate oxidase production is substantially complete, and is usually 10–40 hours.

To separate lactate oxidase from the culture, the cultured mass is filtered or centrifuged to collect the cells, which are disrupted by treatment with mechanical means or enzymes such as lysozyme. Further if necessary lactate oxidase is solubilized by adding ethylenediaminetetraacetic acid (EDTA) and a surfactant such as Triton X-100 (trademark) or Adecatol SO-120 (trademark) to separate the enzyme. The thus-obtained solution of lactate oxidase is treated with or without concentration, and thereafter the enzyme is precipitated by salting out with the addition of a soluble salt such as ammonium sulfate, or is precipitated by adding water miscible organic solvent such as methanol, ethanol, acetone or isopropanol. Low molecular weight impurities are removed by dialysis. Furthermore purification of lactate oxidase is preferably performed by adsorption chromatography or gel filtration. The enzyme solution thus obtained is treated by vacuum concentration, ultra filtration concentration and lyophilization to product powdered lactate oxidase.

Lactate oxidase of the present invention is assayed as follows and has the following physico-chemical properties.

(1) Assay method

| Reaction mixture (1.0 ml): | |
| --- | --- |
| 0.2 M dimethylglutarate-NaOH buffer (pH 6.5) | 0.2 ml |
| 0.5 mM L-lactic acid | 0.1 ml |
| 0.2% (W/V) N,N-dimethylaniline | 0.2 ml |
| 0.2% (W/V) 4-aminoantipyrine | 0.1 ml |
| 45 U/ml peroxidase solution | 0.1 ml |
| distilled water | 0.3 ml |

To the above reaction mixture (1.0 ml) is added lactate oxidase solution (10 μl) and the mixture is incubated at 37° C. for 10 minutes. 1%(W/V) Cation FB-500 (tradename: surfactant) (1.5 ml) is added to stop the reaction, and there is further added distilled water (1.5 ml). The color formed is measured by colorimetric method as 565 nm.

A unit (1 unit, 1 U) of enzyme activity is defined as the activity which generates 1 μmole hydrogen peroxide per minute. The activity is calculated by the following equation:

Enzyme activity (U/ml)=($\Delta A_{565}$/min)×15.5
wherein $\Delta A_{565}$ means absorbency change at 565 nm per minute.

(2) Substrate specificity

In the above assay method, lactic acid in the reaction mixture is replaced by the following substances to determine the substrate specificity of lactate oxidase. Results are shown as relative activity for lactic acid.

| Substrate | Relative Activity (%) |
| --- | --- |
| L-lactic acid | 100 |
| pyruvic acid | 0 |
| DL-α-alanine | 0 |
| succinic acid | 0 |
| maleic acid | 0 |
| L-ascorbic acid | 0 |
| DL-serine | 0 |
| dihydroxyacetone | 2.7 |
| DL-glyceric acid | 0 |

As shown hereinabove the enzyme lactate oxidase has high specificity for L-lactic acid.

(3) Enzyme action

The enzyme catalyzes the oxidative reaction of lactic acid and oxygen to form pyruvic acid and hydrogen peroxide:

$$CH_3CH(OH)COOH + O_2 \rightarrow CH_3COCOOH + H_2O_2$$

(4) Optimum pH

Effect of pH on lactate oxidase activity is measured by assaying an enzyme activity on lactic acid in 40 mM acetate buffer (pH 4–4.5), 40 mM dimethylglutarate-NaOH buffer (pH 4–8), 40 mM phosphate buffer (pH 6.3–8), 40 mM Tris-HCl buffer (pH 7–9) and 40 mM glycine buffer (pH 9–10). Results are shown in FIG. 1 in which optimum pH is pH 6–7.

(5) Optimum temperature

Figure 2:
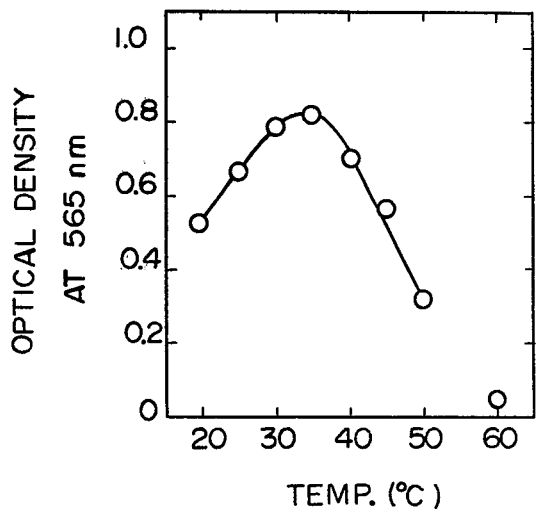
FIG. 2 shows the optimum temperature of lactate oxidase.

Lactate oxidase activity on lactic acid is measured according to the assay method hereinabove. Results is shown in FIG. 2 in which the optimum temperature is about 35° C.

(6) Isoelectric point pH 4.6±0.3 (measured by electrophoresis using carrier ampholite).

(7) Molecular weight 80,000±10,000 (measured by gel filtration method using Sephadex G-150 [tradename, Pharmacia Co.])

40,000±5,000 (measured by SBS-polyacrylamide electrophoresis)

These data suggest that the enzyme of the present invention can be presumed to be the dimer.

(8) pH stability

Figure 3:
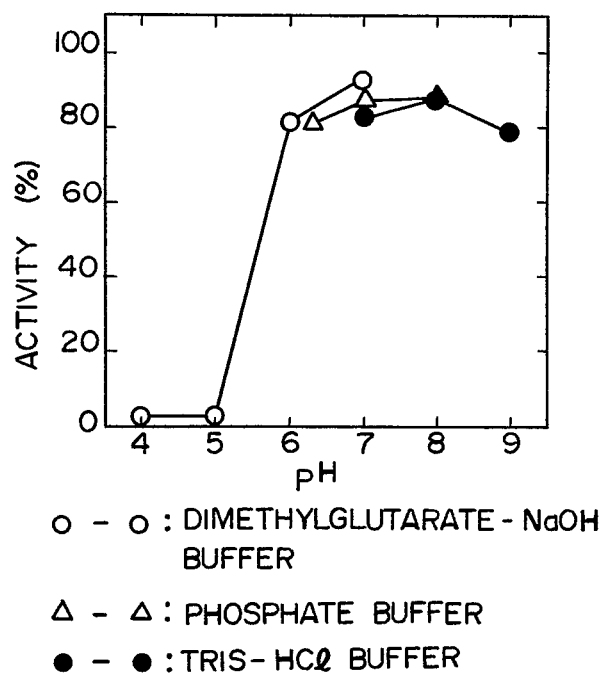
FIG. 3 shows the pH stability of lactate oxidase.

To lactate oxidase (5 μg protein) is added 0.1 M dimethylglutarate-NaOH buffer for pH 4–7 (0.1 ml), 0.1 M phosphate buffer for pH 6.3–8 (0.1 ml) or 0.1 M Tris-HCl buffer for pH 7–9 (0.1 ml), and the mixture is allowed to stand for 10 minutes at 50° C. and cooled with ice. 10 μl of the enzyme solution are taken and enzyme activity is determined. As shown in FIG. 3, the enzyme is stable at pH 6.8–8.5.

(9) Heat stability

Figure 4:
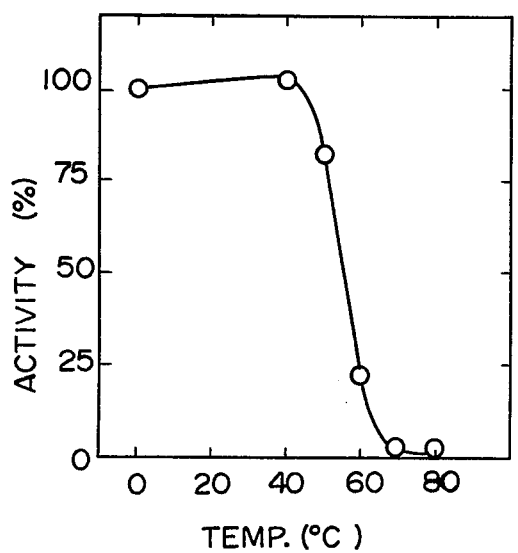
FIG. 4 shows the heat stability of lactate oxidase.

Heat stability of the enzyme is determined by incubating in 0.1 M phosphate buffer (pH 7.0, 0.1 ml) containing the enzyme lactate oxidase (enzyme protein 5 μg) at various temperatures in the range 0°–80° C. for 10 minutes and cooled with ice. 10 μl of enzyme solution are taken and assayed for lactate oxidase activity according to the method hereinabove. As shown in FIG. 4, the enzyme is stable below 40° C. and the activity is rapidly lost above 40° C.

(10) Effect of several substances

The effect of several substances on the enzyme activity is examined by adding the substance indicated below. The amount of addition is 10 mM for metallic salt and EDTA, 0.1% (W/V) for surface active agent, 0.05 mM for p-chloromercuribenzoate (PCMB), 10 μM for flavin adenine dinucelotide (FAD), 0.1 mM for flavin mononucleotide (FMN) and riboflavin.

| Substance added | Relative activity (%) |
| --- | --- |
| No addition | 100.0 |
| $MnCl_2$ | 97.4 |
| $MgCl_2$ | 101.7 |
| $CaCl_2$ | 105.5 |
| $CoCl_2$ | 95.7 |
| LiCl | 95.3 |
| $FeCl_3$ | 8.12 |
| EDTA | 98.0 |
| PCMB | 89.7 |
| FAD | 101.3 |
| FMN | 94.0 |
| Riboflavin | 96.4 |
| Sodium lauryl benzene sulfonate | 21.5 |
| Sodium dodecyl sulfate | 1.8 |
| Adekatol SO-120 (tradename) | 102.8 |
| Triton X-100 (tradename) | 107.2 |
| Bridge-35 (tradename) | 98.2 |
| Cetyltetraammonium bromide | 10.8 |
| Cation FB-500 (tradename) | 3.7 |
| Cation DT-205 (tradename) | 88.6 |

(11) Electrophoresis

Figure 5:
FIG. 5 shows the electrophoresis pattern of lactate oxidase.

Polyacrylamide disc-electrophoresis was carried out using polyacrylamide gel (pH 7.5) and Tris-barbital buffer (pH 7.15) at constant current 4 mA/gel. As shown in FIG. 5 electrophoreted gel stained by amido black is shown as a single dark blue band which shows the enzyme lactate oxidase as a single protein.

(12) Mode of enzyme action:

The assay method of lactate oxidase of the present invention uses a reaction mixture as follows:

| | |
| --- | --- |
| DL-lactic acid or L-lactic acid | 0-0.4 μmole |
| dimethylglutarate-NaOH buffer (pH 6.5) | 40 μmoles |
| 4-aminoantipyrin | 300 μg |
| N,N dimethylaniline | 200 μg |
| peroxidase | 4.5 U |
| lactate oxidase (200 U/mg) | 2 U |

The above reaction mixture (1.0 ml) is incubated at 37° C. for 10 minutes, and thereafter is added 1% (W/V) cation FB-500 (tradename) (0.5 ml) solution and distilled water (1.5 ml). The color formed is measured by colorimetric method at 565 nm.

Standard curve is prepared by adding hydrogen peroxide in place of lactic acid.

Figure 6:
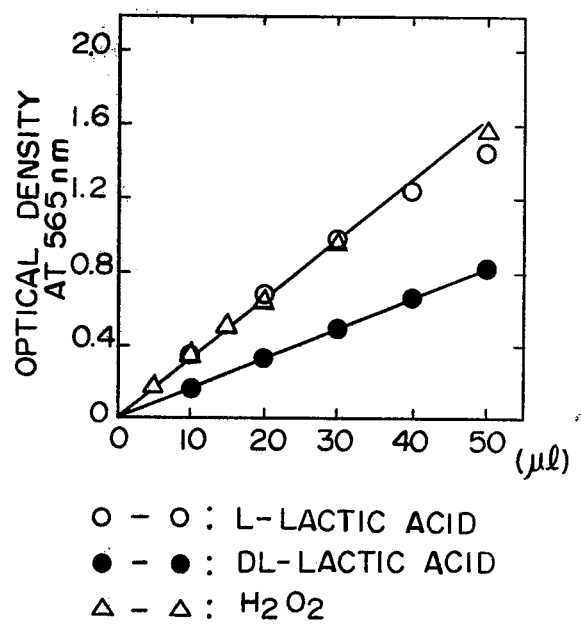
FIG. 6 shows the results of measuring hydrogen peroxide formation by lactate oxidase, wherein standard curves represent various substrates or the substrate is replaced by hydrogen peroxide.

As shown in FIG. 6, wherein o—o indicates L-lactic acid used as substrate, •—• shows D-lactic acid used as substrate and Δ—Δ shows hydrogen peroxide used instead of a substrate, the enzyme lactate oxidase of the present invention catalyzes the reaction which forms one mole of L-lactic acid.

Further, oxygen consumption is measured by oxygen-electrode (YSI-dissolved oxygen meter), and one mole of oxygen is consumed by oxidation of one mole of lactic acid.

Pyruvic acid formed is confirmed by the following method.

A reaction mixture (1.0 ml) consisting of dimethylglutarate-NaOH buffer (40 μmoles), catalase (400 μg), L-lactic acid or DL-lactic acid (0-0.5 μmole) and lactate oxidase (2 U) is incubated at 37° C. for 10 minutes. The reaction mixture is heated in boiling water for 5 minutes to stop the reaction. After ice-cooling, 10 mM $NADH_2$ (0.1 ml) and distilled water (1.9 ml) are added therein, and denatured protein is removed by centrifuge. The supernatant solution (2.5 ml) is taken up in a quartz cell, preincubated at 37° C., and lactate dehydrogenase (20 U, bovine liver, Boehlinger Mannheim G.m.b.H.) solution (5 ml) is added thereto. It is incubated at 37° C. for 5 minutes and measured by colorimetric method at 340 nm. The standard curve is prepared by adding pyruvic acid in place of L-lactic acid.

Figure 7:
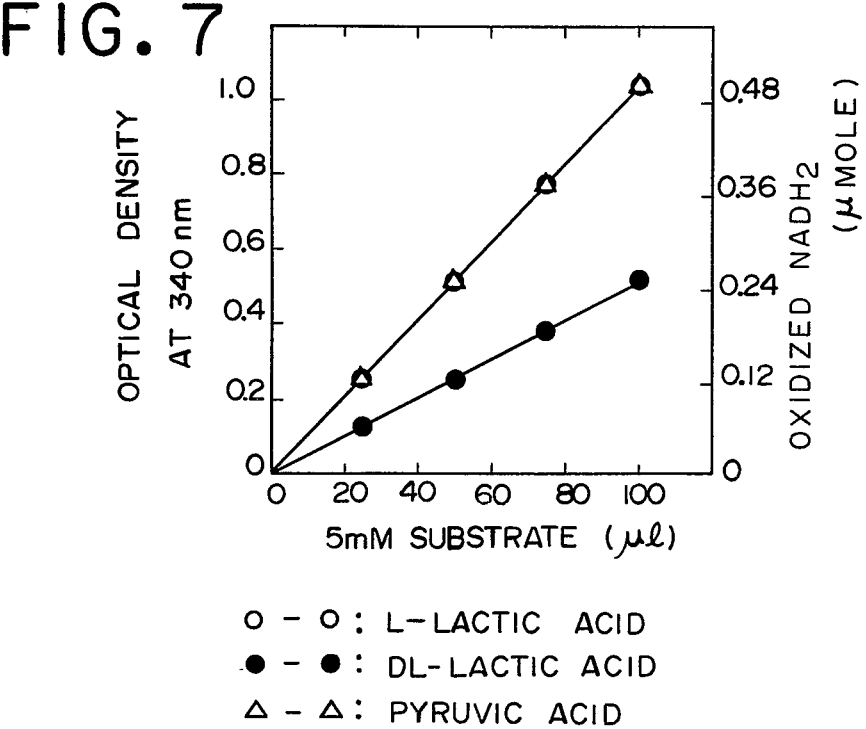
FIG. 7 shows the results of quantitative analysis of pyruvic acid formation by lactate oxidase wherein standard curves represent various substrates or the substrate is replaced by pyruvic acid.

As shown in FIG. 7, o—o shows that L-lactic acid is used as substrate, •—• shows that DL-lactic acid is used as substrate and Δ—Δ shows that pyruvic acid is used in place of a substrate.

The above reaction mixture (1.0 ml) is incubated at 37° C. for 10 minutes, and the thus-formed α-keto acid is measured by the hydrazide method using 2,4-dinitrophenylhydrazine. One mole of α-keto acid is formed from one mole of L-lactic acid. As a result, the enzyme lactate oxidase of the present invention acts on L-lactic acid, and catalyzes the reaction which forms one mole of pyruvic acid and consumes one mole of oxygen.

As hereinabove explained, the enzyme lactate oxidase of the present invention reacts directly on lactic acid with oxygen and does not require a coenzyme for the oxidation of L-lactic acid to form pyruvic acid and hydrogen peroxide. Furthermore, the physico-chemical properties of the enzyme of the present invention such as isoelectric point of pH 4.6, molecular weight of 80,000±10,000, and the like, indicate the differences from the prior known lactate oxidase; and hence the lactate oxidase of the present invention is confirmed as a novel enzyme.

In the above confirmation test for the mode of action of lactate oxidase, the quantitative analysis for liberated hydrogen peroxide, pyruvate and consumed oxygen is one of the examples of L-lactic acid analysis. We have also found that the lactate oxidase can be used for the novel quantitative analysis of L-lactic acid comprising assaying generated hydrogen peroxide and pyruvic acid and consumed oxygen, and in a kit for lactic acid analysis. The novel analytical method for L-lactic acid and a kit for L-lactic acid analysis can be used for measuring the purity of a lactic acid reagent, or for the quantitative determination of lactic acid in serum, the analysis of lactic acid derivative comprising liberating a lactic acid by decomposition thereof, and the activity of an enzyme which liberates lactic acid, and a kit for analysis thereof.

Therefore this invention includes an analytical method for determining lactic acid in a sample which comprises incubating lactate oxidase in a sample containing lactic acid and measuring the thus-generated hydrogen peroxide and pyruvic acid or consumed oxygen, and a kit for lactic acid analysis in a sample comprising a reaction system at least containing lactate oxidase.

Any samples which contain lactic acid as a substrate for lactate oxidase can be analyzed. For example, lactic acid samples, medicaments containing lactate such as calcium lactate and ferrous lactate, lactic acid in serum, lactic acid fermentation products of lactic acid bacteria such as *Lactobacillus plantarum* and *Pediococcus lindneri*, the quantitative analysis of pyruvic acid in a sample which comprising lactic acid formation by reacting with pyruvic acid and lactate dehydrogenase, and enzyme activity assays or quantitative analyses of lactate dehydrogenase can be mentioned. These examples can be analyzed in an aqueous medium, preferably in a buffer solution at pH 6-7.

The amount of lactate oxidase can be selected from substantial enzyme reaction which oxidizes lactic acid in a sample. For example, two units of lactate oxidase can preferably be used. The enzyme can be used in itself or in a buffer solution or in lyophilized form. Lactate oxidase can be in a microcapsulated form or in an immobilized form of covalent linkage with an organic or inorganic carrier or adsorbed on a carrier.

Assay is performed by incubation with the sample and lactate oxidase. Incubation time and temperature can be selected for substantial enzyme reaction, preferably for 5-30 minutes and at 35°-37° C. As a result, hydrogen peroxide and pyruvic acid are generated in the sample and oxygen is consumed. Then hydrogen peroxide, pyruvic acid or oxygen is measured.

Oxygen can be measured most simply by oxygen electrode. Pyruvic acid can be measured by applying the lactate dehydrogenase method or hydrazone method. Furthermore, pyruvic acid can be analyzed by a reaction mixture comprising a specific enzyme for pyruvate such as pyruvate oxidase (150 U/ml, 20 μl), 10 mM thiamine pyrophosphate (20 μl), 1 mM FAD (10 μl), 10 mM MnCl$_2$ (50 μl), peroxidase (45 U/ml, 0.1 ml), 0.2% N,N-dimethylaniline (0.2 ml), 0.3% 4-aminoantipyrine (0.1 ml) and 0.1 M phosphate buffer (pH 7.5, 0.1 ml).

Hydrogen peroxide can be analyzed by hydrogen peroxide electrode or colorimetric method comprising an indicator system of one or more chromogens which is effected by coupling with hydrogen peroxide. Examples of such indicators are combinations of tetravalent titanium compounds and xylenol orange which couples with hydrogen peroxide to form a stable red color, or a combination of phenol or N,N-dimethylaniline, 4-aminoantipyrin and peroxidase for measuring color. Furthermore, in the reaction system of a combination of phenol or N,N-dimethylaniline, 4-aminoantipyrin and peroxidase, the amount of phenol or N,N-dimethylaniline is about 0.005-0.05% and the amount of 4-aminoantipyrin is more than equimolar, preferably in two molar excess of the generated hydrogen peroxide, and the amount of peroxidase can be over 1 U. The thus-prepared indicator can optionally be prepared with lactate oxidase, or 0.01-1 mM of PCMB can also be added therein. The color thus formed is measured by colorimetry with a suitable wave length and the generated hydrogen peroxide can be measured by calculation from the corresponding standard curve. The addition of PCMB is effective for stabilization of color upon serum assay.

As hereinabove explained, the analytical method using the prepared novel lactate oxidase of the present invention and a kit for analysis can advantageously be used, by measuring the generated hydrogen peroxide, pyruvic acid or consumed oxygen, for the quantitative analysis of lactic acid in serum, or a purity test of a lactic acid reagent, or the quantitative analysis of lactic acid in lactic acid fermentation, or for an enzyme for which lactic acid acts as a substrate.

The following examples illustrate the embodiments of the present invention but are not to be construed as limiting the invention. In the examples, all percentages are indicated as W/V%.

EXAMPLE 1

Four samples of culture medium (each 100 ml, pH 7) comprising glucose (2%), peptone (1%), yeast extract (0.5%), NaCl (0.2%), KH$_2$PO$_4$ (0.1%), K$_2$HPO$_4$ (0.1%), MgSO$_4$7H$_2$O (0.05%) and CaCO$_3$ (0.3%) in a 500 ml Erlenmyer flask were sterilized at 120° C. for 20 minutes. To each medium was inoculated a strain of Pediococcus sp. B-0667 FERM-P No. 4438, Streptococcus sp. B-0668 FERM-P No. 4439, *Aerococcus viridans* IFO-12219 or *Aerococcus viridans* IFO-12317, respectively and shake-cultured at 30° C. for 15 hours, at 300 r.p.m. Thereafter cultured cells centrifugally collected were washed with 10 mM phosphate buffer (pH 6.5) and again centrifuged to collect bacterial cells. The thus-obtained cells were suspended in 10 mM phosphate buffer (10 ml, pH 8.0) containing 0.02% lysozyme and 0.1% Triton X-100 and incubated at 37° C. for 60 minutes. The supernatant obtained centrifugally which contains lactate oxidase was collected. Enzyme activity of the supernatant is shown in the following table.

| Strain | Enzyme activity (U/ml) |
|---|---|
| B-0667 | 0.24 |
| B-0668 | 0.31 |
| IFO-12219 | 0.42 |
| IFO-12317 | 0.43 |

EXAMPLE 2

A medium (20 l.) consisting of the same components as described in Example 1 in a 30 l. jar-fermenter adding 0.1% concentration of disform BC-51Y (tradename) was sterilized by steam. Cultured broth (200 ml) of Pediococcus sp. B-0667 FERM-P No. 4438 cultured the same way as in Example 1 was transferred thereto, and cultured at 30° C. for 15 hours. Bacterial cells centrifugally collected (about 400 g) were suspended in lysozyme solution (0.2 mg/ml, 4 l.), and there was further added Triton X-100 (trademark, 4 g), EDTA (3 g) and 1 M phosphate buffer (pH 8, 40 ml) and the mixture was stirred at 37° C. for 60 minutes to disrupt cells. To the supernatant obtained centrifugally (3.7 l., 5200 U) was added acetone (1.48 l.) and the precipitated impurity was removed by centrifugation. To the supernatant was added acetone up to 65% concentration. The precipitate obtained by centrifugation at 5000 r.p.m. for 10 minutes, was dissolved in 10 mM phosphate buffer (pH 7, 400 ml) and the impure precipitate was separated by centrifugation. Saturated ammonium sulfate (470 ml) was then added and stirred for 20 minutes and the precipitate, which was collected by centrifugation at 12000 r.p.m. for 10 minutes, was dissolved in 10 mM phosphate buffer (pH 7, 100 ml). The solution was dialyzed against 10 mM phosphate buffer overnight and passed through a column (2.6×50 cm) of DEAE-cellulose buffered at pH 7 to absorb the enzyme, then gradiently eluted with 0.1-0.6 M KCl. Fractions eluted at about 0.5 M KCl were collected to obtain the enzyme active fraction (140 ml).

To the solution was added saturated ammonium sulfate (185 ml) and the precipitate was removed centrifugally. To the supernatant solution was added saturated ammonium sulfate solution (145 ml) and the precipitate was collected centrifugally.

After dissolving the precipitate in 10 mM phosphate buffer (pH 7.0, 50 ml) and dialyzing to desalt it, the solution was charged on a column of DEAE-Sephadex A-50 (trademark) (2.6×50 cm) buffered with 10 mM phosphate buffer to absorb the enzyme and the fractions were gradiently eluted over the range 0.2–0.6 M KCl. Fractions eluted by 0.5 M KCl were collected (160 ml) and dialyzed to desalt them and lyophylized. The lyophilized powder was dissolved in a mixture of 10 mM phosphate buffer (pH 7.0, 5 ml) and 0.1 M KCl and chromatographed on a column of Sephadex G-150 (trademark) (2.5×73 cm, flow rate 8 ml/min., 5.2 ml/fraction). Active fractions No. 27–35 were collected, desalted by dialysis and lyophilized. The lyophilized enzyme appeared as a single band upon electrophoresis as hereinbefore explained. The purification schema was shown below.

|  | Total Protein (mg) | Total Activity (U) | Specific Activity (U/mg) |
|---|---|---|---|
| Cell extract | 34040 | 5200 | 0.028 |
| Acetone precipitate | 3652 | 4780 | 1.31 |
| 1st ammonium sulfate precipitate | 2378 | 4590 | 1.93 |
| DEAE-cellulose | 663 | 3672 | 5.80 |
| 2nd ammonium sulfate precipitate | 163 | 3253 | 19.9 |
| DEAE-Sephadex A-50 | 44.7 | 2667 | 59.7 |
| Sephadex G-150 | 13.07 | 2614 | 200 |

EXAMPLE 3

Quantitative determination of L-lactic acid:

| Reaction mixture: | |
|---|---|
| 0.2 M dimethylglutarate-NaOH buffer | 0.2 ml |
| peroxidase (45 U/ml) | 0.1 ml |
| 0.3% 4-aminoantipyrin | 0.1 ml |
| 0.2% N,N-dimethylaniline | 0.2 ml |
| 5 mM L-lactic acid or 5 mM DL-lactic acid | 0–80 μl |
| Add distilled water to total volume of 1 ml. | |

To the above reaction mixture (1 ml) was added L-lactate oxidase solution (100 U/ml, 20 μl), incubated at 37° C. for 20 minutes and 1% Cation FB-500 (tradename, 0.5 ml) was added, as well as distilled water (1.5 ml). The color formed was measured by the colorimetric method at 565 nm. The result was identical with the amount of lactic acid measured by a standard curve of hydrogen peroxide hereinabove.

EXAMPLE 4

A composition for lactic acid analysis by colorimetric assay comprises the following:

| 0.1 M dimethylglutarate-NaOH buffer | 10 ml |
|---|---|
| peroxidase (45 U/ml) | 5 ml |
| 0.3% 4-aminoantipyrin | 5 ml |
| lactate oxidase (100 U/ml) | 1 ml |
| sucrose | 20 mg |

The above mixture is lyophilized at −40° to −50° C., at 0.01–0.05 mmHg for 3 hours to prepare the reagent (A) of the kit for lactate analysis (for 50 ml preparation). Additional aqueous solution (5 ml) comprising 0.2% N,N-dimethylaniline containing 8 μmole PCMB was included.

To the reagent (A) of the kit is added all the additional solution and distilled water is also added to prepare 50.0 ml solution. The thus-prepared reagent solution is used for analysis in the amount of 1.0 ml per test.

EXAMPLE 5

Each aliquot solution (1.0 ml) of the reagent solution for lactic acid anlysis was put in reaction vessels. Thereto was added 5 mM DL-lactic acid solution (each 0-100 μl) (for control), or 2.5 mM hydrogen peroxide (each 0-100 μl) for calibration curve by hydrogen peroxide), or human serum (each 0-100 μl), or human serum (50 μl) along with 5 mM DL-lactic acid (each 0-100 μl), and the mixtures were incubated at 37° C. for 20 minutes. 1% Cation FB-500 (tradename, 0.5 ml) and distilled water (1.5 ml) were added to each and the absorbency at 565 nm was measured by colorimetry.

Figure 8:
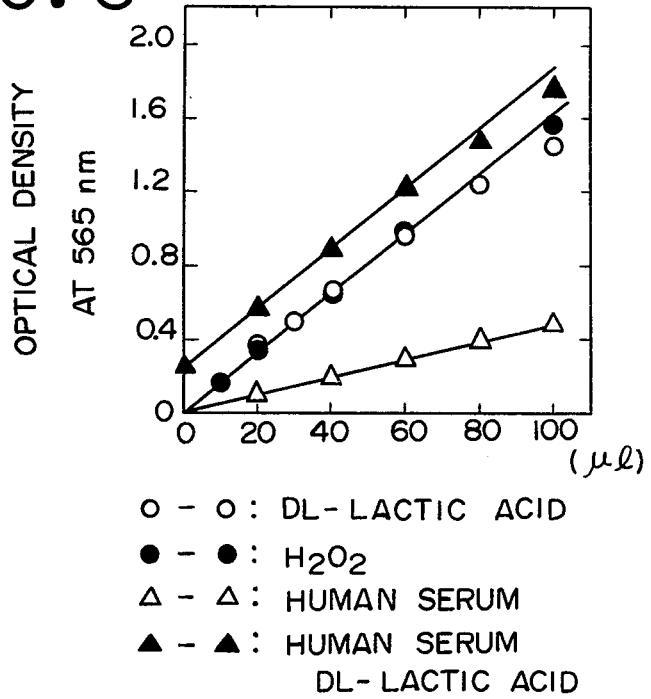
FIG. 8 shows the results of quantitative analysis of serum lactic acid using lactate oxidase and various substrates.

As shown in FIG. 8, wherein o—o indicates the control by DL-lactic acid, •—• indicates the calibration curve by hydrogen peroxide, Δ—Δ indicates the amount of lactic acid in human serum measured by the amount of hydrogen peroxide, and ▲—▲ indicates the amount of lactic acid in human serum with the addition of DL-lactic acid, good quantitative results were observed in the assay of the lactic acid in human serum and serum to which is added lactic acid.

What is claimed is:

1. An enzyme lactate oxidase having at least the following substrate specificity and enzyme action:
    substrate specificity: L-lactic acid
    enzyme action: catalyzes the reaction L-lactic acid + O$_2$ → pyruvic acid + H$_2$O$_2$.

2. An enzyme lactate oxidase as claimed in claim 1 in which the said enzyme has an optimum pH of pH 6-7, an optimum temperature of about 35° C., an isoelectric point of pH 4.6±0.3 (measured by electrophoresis using carrier ampholite), and a molecular weight of 80,000±10,000.

3. A process for the manufacture of lactate oxidase having substrate specificity at least for L-lactic acid and catalyzing the reaction L-lactic acid + O$_2$ → pyruvic acid + H$_2$O$_2$ which comprises culturing a lactate oxidase-producing microorganism belonging to a genus selected from, Pediococcus sp. B-0667, Streptococcus sp. B-0668, *Aerococcus viridans* IFO-12219 and *Aerococcus viridans* IFO-12317, in a nutrient culture medium, and isolating the lactate oxidase thus produced from the cultured medium.

4. A process as claimed in claim 3 in which the said lactate oxidase has an optimum pH of pH 6–7, an optimum temperature of about 35° C., an isoelectric point of pH 4.6±0.3 (measured by electrophoresis using carrier ampholite), and a molecular weight of 80,000±10,000.

5. A method for the analysis of lactic acid in a sample containing lactic acid or a lactic acid-liberating system, comprising contacting said sample with lactate oxidase having substrate specificity at least for L-lactic acid and an enzyme action catalyzing the reaction L-lactic acid + O$_2$ → pyruvic acid + H$_2$O$_2$, and measuring generated hydrogen peroxide, pyruvic acid or consumed oxygen.

6. A method as claimed in claim 5, in which said lactate oxidase has an optimum pH of ph 6–7, an optimum temperature of about 35° C., an isoelectric point of pH 4.6±0.3 (measured by electrophoresis using carrier ampholite), and a molecular weight of 80,000±10,000.

7. A kit for the analysis of lactic acid, which comprises a system containing at least lactate oxidase having substrate specificity at least for L-lactic acid and an enzyme action catalyzing the reaction $$\text{L-lactic acid} + O_2 \rightarrow \text{pyruvic acid} + H_2O_2.$$

8. A kit as claimed in claim 7, in which said lactate oxidase has an optimum pH of pH 6–7, an optimum temperature of about 35° C., an isoelectric point of pH 4.6±0.3 (measured by electrophoresis using carrier ampholite), and a molecular weight of 80,000±10,000.

9. A kit as claimed in claim 7, comprising at least a combination of lactate oxidase and an indicator for hydrogen peroxide.

10. A kit as claimed in claim 9, in which said indicator for hydrogen peroxide comprises at least 4-aminoantipyrin, N,N-dimethylaniline and peroxides.

* * * * *

Notice of Adverse Decision in Interference

In Interference No. 100,995, involving Patent No. 4,237,222, H. Misaki, Y. Horiuchi, K. Matsuura and S. Harada, LACTATE OXIDASE PROCESS FOR THE MANUFACTURE THEREOF AND ANALYTICAL METHOD AND KIT FOR THE USE OF THE SAME, final judgment adverse to the patentees was rendered Jan. 17, 1984, as to claim 1.

[*Official Gazette March 13, 1984.*]

Disclaimer 4,237,222.—*Hideo Misaki; Yoshifumi Horiuchi; Kazuo Matsuura* and *Saburo Harada,* Shizuoka, Japan. LACTATE OXIDASE PROCESS FOR THE MANUFACTURE THEREOF AND ANALYTICAL METHOD AND KIT FOR THE USE OF THE SAME. Patent dated Dec. 2, 1980. Disclaimer filed Mar. 20, 1984, by the assignee, *Toyo Jozo Kabushiki Kaisha.*

Hereby enters this disclaimer to claims 1, 2 and 5–10 of said patent.
[*Official Gazette May 15, 1984.*]